United States Patent [19]
Bonassa et al.

[11] Patent Number: 5,303,699
[45] Date of Patent: Apr. 19, 1994

[54] INFANT VENTILATOR WITH EXHALATION VALVES

[75] Inventors: Jorge Bonassa; Mario Amato; Milton R. Salles, all of Sao Paulo, Brazil

[73] Assignee: Intermed Equipamento Medico Hospitalar Ltda., Sao Paulo, Brazil

[21] Appl. No.: 792,868

[22] Filed: Nov. 18, 1991

[51] Int. Cl.[5] .............................. A61M 16/00
[52] U.S. Cl. ................... 128/204.21; 128/204.23; 128/204.24; 128/204.25; 128/204.26; 128/205.23; 128/205.24
[58] Field of Search ............. 128/204.21, 204.23, 128/204.24, 204.25, 204.26, 205.23, 205.24, 203.12

[56] References Cited

U.S. PATENT DOCUMENTS

| | | | |
|---|---|---|---|
| 4,538,604 | 9/1985 | Usry et al. | 128/204.23 |
| 4,747,403 | 5/1988 | Gluck et al. | 128/204.21 |
| 4,838,257 | 6/1989 | Hatch | 128/204.21 X |
| 4,982,735 | 1/1991 | Yagata et al. | 128/204.21 X |
| 5,048,515 | 9/1991 | Sanso | 128/204.21 X |
| 5,050,593 | 9/1991 | Poon | 128/204.23 |
| 5,074,299 | 12/1991 | Dietz | 128/204.21 |

Primary Examiner—Vincent Millin
Assistant Examiner—Raleigh W. Chiu
Attorney, Agent, or Firm—Ladas & Parry

[57] ABSTRACT

A ventilator device for artificial ventilation use in infant and pediatric wards, and which may be adapted for use with adult patients as well. The ventilator device comprises a pressure control system having at least two parallel connected exhalation valves, a pressure monitoring system having bar display, optical sensors attached to the bar display, and an alarm system with a "no break" system including a rechargeable battery. One of the exhalation valves is connected at the beginning of the inspiratory airway and this valve is coupled with a moisturizing system. An inspiratory tube connected to the moisturizing system is connected to one branch of a "Y" connector where the other branch of the "Y" connector is connected to an expiratory tube leading to the other exhalation valve at the end of the expiratory airway. These exhalation valves are controlled by electronic control modules and pneumatic control through 3-way 2-position solenoid valves. These devices are capable of controlling pressure, controlling inspiratory and expiratory times, and regulating and monitoring the ratio between the inspiratory and the expiratory times. The ventilator is particularly effective in that it is capable of controlling pressure in the event of an obstruction which often increases the pressure above a safe limit, thus possibly resulting in rupturing of the lungs. The device is capable of providing a continuous flow with timed cycles and pressure control in order to guard against a sudden increase or decrease of pressure in the ventilator.

13 Claims, 5 Drawing Sheets

INFANT VENTILATOR WITH EXHALATION VALVES

BACKGROUND OF THE INVENTION

1. Field of the Invention

The present invention is related to an infant ventilator for artificial ventilation used in different situations in neonatal and pediatric wards, as well as to exhalation valves used in such a device. The invention can be used whenever there is a need to maintain a constant respiratory activity in a patient by means of mechanical ventilation.

2. Brief Description of the Prior Art

Modern ventilators used for pediatric and neonatal care are of continuous flow, with limited time cycles and pressure. In this type of ventilator, a preset mixture of air and oxygen flows continuously and constantly through a tube known as an inspiratory tube until it reaches the patient. This mixture of air passes through a moisturizing system, and from this system, through another tube called an expiratory tube, to an exhalation valve at the end of the expiratory airway. During the inspiratory phase, the valve is opened during expiration and closed during inspiration. This allows a continuous flow of the mixture to pass through the tubes to the patient, or, during the expiratory phase, to the environment when the air accumulated in the lungs during the inspiratory phase is exhaled together with the continuous flow.

While closed, the exhalation valve maintains a closing pressure or an inspiratory pressure which may be adjusted, in order to maintain a constant limited pressure in the patient's system during the inspiratory phase. Thus, while open, it is possible to maintain an expiratory pressure, also adjustable, defining a residual pressure during expiration within desired preset limits.

The duration of inspiratory and expiratory phases is obtained through electronic circuits and/or pneumatic circuits which open and close the exhalation valve. The exhalation valve at the end of the expiratory airway is the active element responsible for the morphologies, pressure levels, and switching of the inspiratory and expiratory phases.

In addition to the essential devices necessary to operate the ventilator, according to the technique hereinabove described, prior art ventilators include systems for monitoring and/or controlling pressure, inspiratory and expiratory times, the ratio between inspiratory and expiratory times, etc. Each model is equipped with an alarm system. These alarm systems range from basic to complex. The basic alarm system is capable of detecting the drop in an inspiratory pressure where the complex alarm system is capable of measuring the minimum and the maximum inspiratory pressure and the time of apnea.

The ventilators currently available have some inherent problems. During the expiratory phase, the patient exhales air accumulated in his lungs during the inspiratory phase, and this air is exhausted together with the air flowing continuously through the system. During expiration, the resistances of the expiratory tube and of the exhalation valve itself result in a residual pressure which is relatively high due to the increased flows employed, to the point of not being able to reduce to atmospheric pressure even during a long expiration. The common solution for this problem is to install a venturi system at the end of the expiratory airway.

To reduce residual pressure, the state of the art ventilators employ an offsetting subatmospheric pressure, promoting a more efficient exhalation through the expiratory airway. In spite of obtaining a baseline with no residual pressure, the use of venturi is known to cause fluctuations in the pressure curves when switching phases. These fluctuations introduce a characteristic noise in the system during the valve's functioning.

As noted, the state of the art ventilators have an exhalation valve placed at the end of the expiratory airway, which effectively controls the pressures in the system. The pressure control is directly affected by the flow and resistance of the respiratory system components, as there already exists a pressure differential between the patient's connection and the end of the expiratory airway, due to the flow and resistance of the expiratory airway. In addition, higher flows generate higher turbulence which affect the valve control.

Another shortcoming of the use of a single valve at the end of the expiratory airway is the total loss of pressure control whenever there is an obstruction in the tubes of the expiratory airway, which will be reflected in an increase of the working pressure over the patient. A severe obstruction will increase the pressure above safety limits capable of rupturing the walls of the lungs, i.e., the occurrence of a pneumothorax. This is one of the most feared problems in neonatal care. In order to solve this problem, the state of the art ventilators use preset or adjustable relief valves which limit the highest pressure in the respiratory system. These valves need to be adjusted before the ventilator is used. However, according to medical statistics, this does not always happen.

SUMMARY OF THE INVENTION

Bearing in mind the problems prior art ventilators have, an improved ventilator having continuous flow with time cycles and limited pressure has been developed. It encompasses other technical features not foreseen in state of the art ventilators.

The present invention is suitable for neonatal and pediatric uses, as well as for adult patients. The present invention may work in one of two ways: controlled intermittent and continuous pressure. In the controlled intermittent mode, the device oscillates between expiratory and inspiratory pressures at set times. In the continuous pressure mode, a constant pressure is maintained against the patient's spontaneous breathing.

The invention includes a system with a double exhalation valve for pressure control in a patient's system, with a precision and safety level superior to the available state of the art devices. The invention also includes a pressure monitoring system utilizing a par display under which optical sensors are positioned, thus allowing optical coupling of the alarm system. The invention also includes a "no break" system with rechargeable battery.

BRIEF DESCRIPTION OF THE DRAWING

In order to allow a better understanding of the present invention, the figures below will be carefully described.

DETAILED DESCRIPTION OF THE PREFERRED EMBODIMENTS

Figure 1:
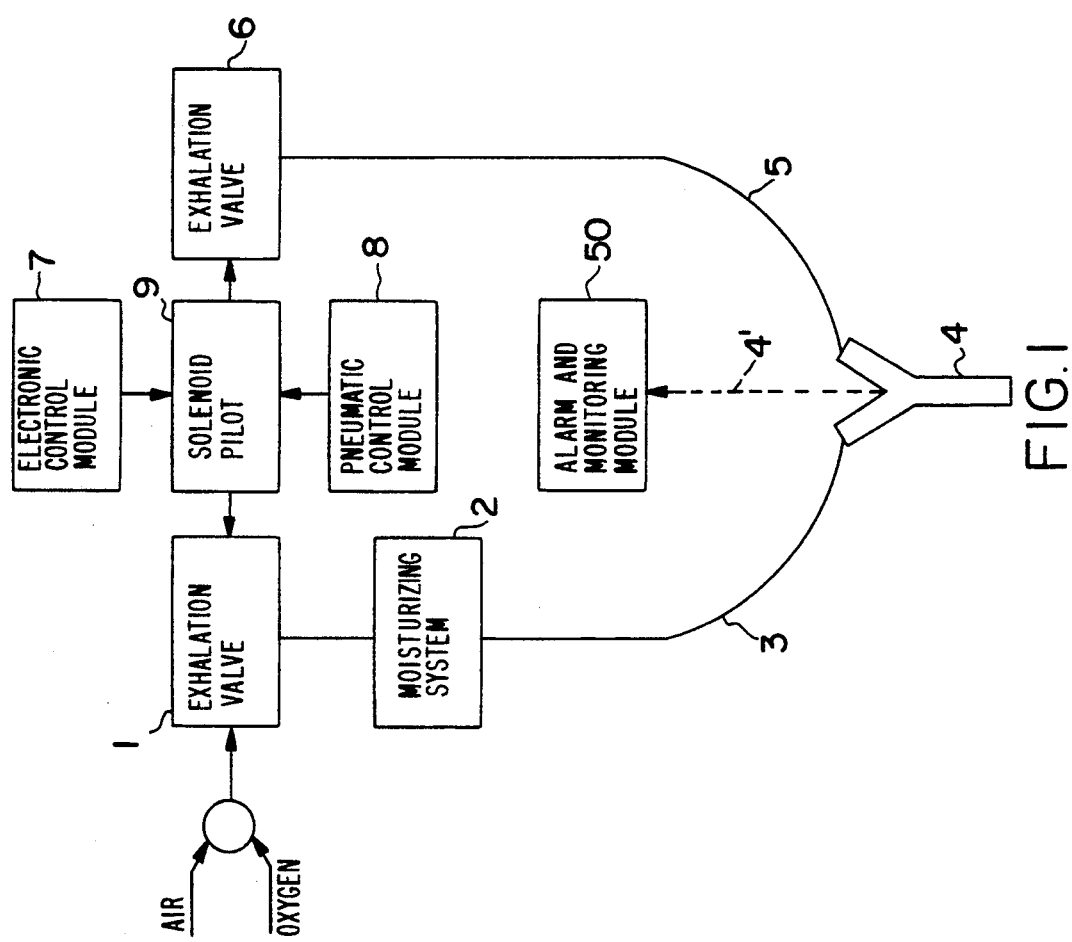
FIG. 1 shows functional diagram of the ventilator according to the present invention.

FIG. 1 illustrates the functional parts of the ventilator, showing a mixture of air and oxygen, previously adjusted by adequate valving (not shown), flowing continuously through the patient's system. This mixture of gases initially passes through the exhalation valve 1 of the expiratory airway, through the moisturizing system 2, the inspiratory tube 3, then into the "Y" connection 4 which is attached to the patient. From the patient, the gas flows through the expiratory tube 5 to the environment through the exhalation valve 6 of the expiratory airway.

The combination of electronic control module 7 and pneumatic control module 8 controls valves 1,6. The pressure monitoring and alarm systems are independent of the control modules, and are included in the alarm and monitoring module 50. The pressure signal is passed from the "Y" connection to the alarm and monitoring module 50 through a tube 4'.

The electronic control module 7 uses a microprocessor and basically controls the inspiratory time and the frequency of the respiratory cycles through two potentiometers (not shown) located on the ventilator's control panel (not shown). The electronic control module 7 thus controls the opening and closing of valves 1 and 6, through the help of a 3-way 2-position solenoid valve 9 having three ways and two set positions. The set values are presented on a lighted display (not shown), together with the values calculated for expiratory time and the ratio between inspiratory and expiratory times. Moreover, the microprocessor control activates a light indicating the inspiratory cycle and another light indicating the inversion ratio between inspiratory/expiratory times. If the ratio between these times exceeds 3:1, the microprocessor will activate a sound alarm and cause the visual inversion ratio indicator to flash intermittently.

Figure 2:
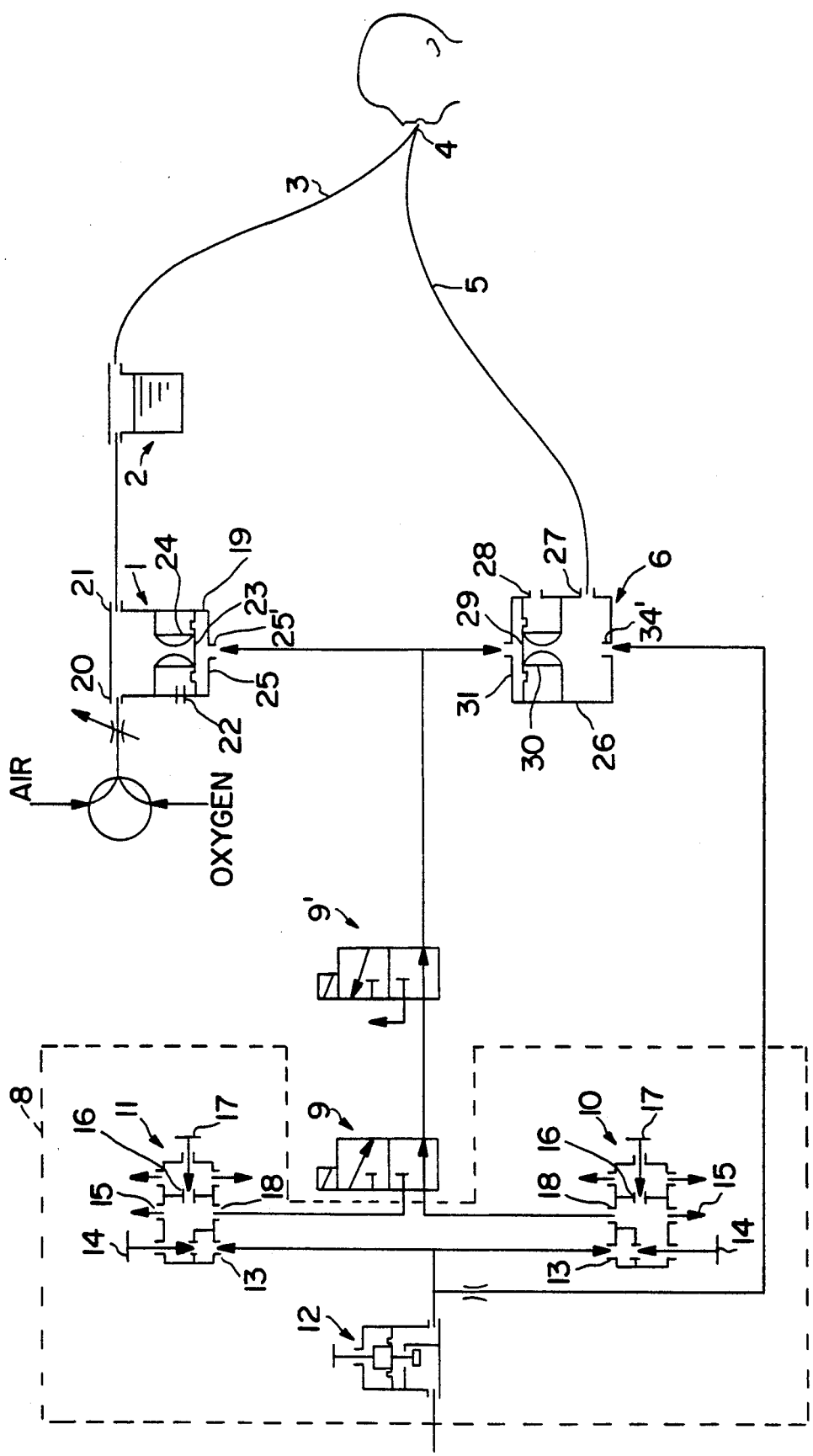
FIG. 2 shows a pneumatic diagram of the pneumatic control module.

The pneumatic control module 8 shown in FIG. 2 allows the control of expiratory and inspiratory pressures through the setting of two knobs (not shown) located on the ventilator panel. This control is basically made by the union of two control valves 10 and 11 for the expiratory pressure and inspiratory pressure, respectively, linked to exhalation valves 1 and 6 through solenoid pilot valve 9 and the solenoid safety shut-off 9'. Basically, it comprises a regulating pressure valve 12 which continually feeds the two valves 10, 11 for the control of the expiratory pressure and inspiratory pressure, respectively, which differ only in their gauges.

Figure 3:
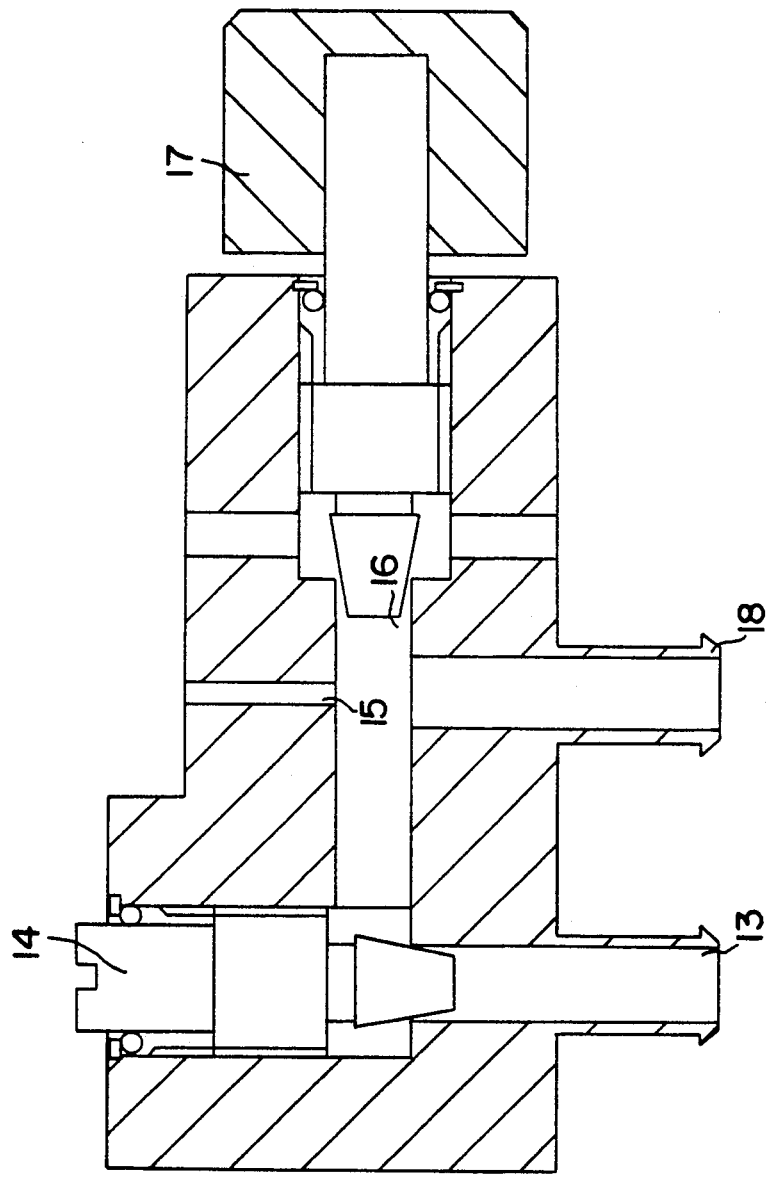
FIG. 3 is a cross-sectional view of the pressure control valve.

These valves, 10, 11, illustrated in FIGS. 2 and 3, show an opening 13 at the entry which is adjustable by means of a bolt 14, supplying a constant flow which is divided in three different ways. The first is a gauged opening 15 which opens to the environment; the second opening 16 is adjustable by the operator with a knob 17 in the panel; and the third, a discharge opening 18, is linked to valves 1 and 6 through solenoid pilot valve 9 and solenoid safety shut-off valve 9'. The lower the discharge allowed to the environment, the higher the pressure will be at the exhalation valves 1 and 6. The expiratory pressure control valve 10 is linked to the normally open route of the solenoid pilot valve 9, and the inspiratory pressure control valve 11 is linked to the normally closed route. Therefore, when the microprocessor sends a signal which energizes and switches on the solenoid pilot valve 9, the inspiratory pressure is applied through pilot valve 9, and the expiratory pressure is no longer maintained.

The pilot pressure from the pilot solenoid 9 is transmitted to the exhalation valves 1 and 6 through the normally open airway of the safety solenoid shut-off valve 9' having three ways and two positions. The other, normally closed route of the safety solenoid 9', is linked to atmospheric pressure. Therefore, when energized, the safety solenoid valve 9' sends atmospheric pressure to the exhalation valves 1 and 6 instead of the pilot pressure. The safety solenoid 9' is activated through a signal from the alarm system when the maximal limit of the inspiratory pressure is reached. In this event, the pilot feeding of the exhalation valves 1 and 6 will be shut off which results in a total depressurization of the patient's respiratory system.

In order to control the pressure at both ends of the respiratory system, two exhalation valves were developed, one, valve 1, located at the beginning of the inspiratory route, and the other, valve 6, at the end of the expiratory route. Both valves are activated by the same pilot pressure coming from pressure control valves 10 and 11 through the solenoid 9, and both basically have the same flow passage dimensional features. However, the first valve 1 is a passage and boost pressure relief valve, whereas the second valve 6 is an exhalation valve for primary pressure control. The joint working of these two valves, together with the specific features of each one of them, detailed next, provide precise and safe control over the working pressure exerted over the patient.

Figure 4:
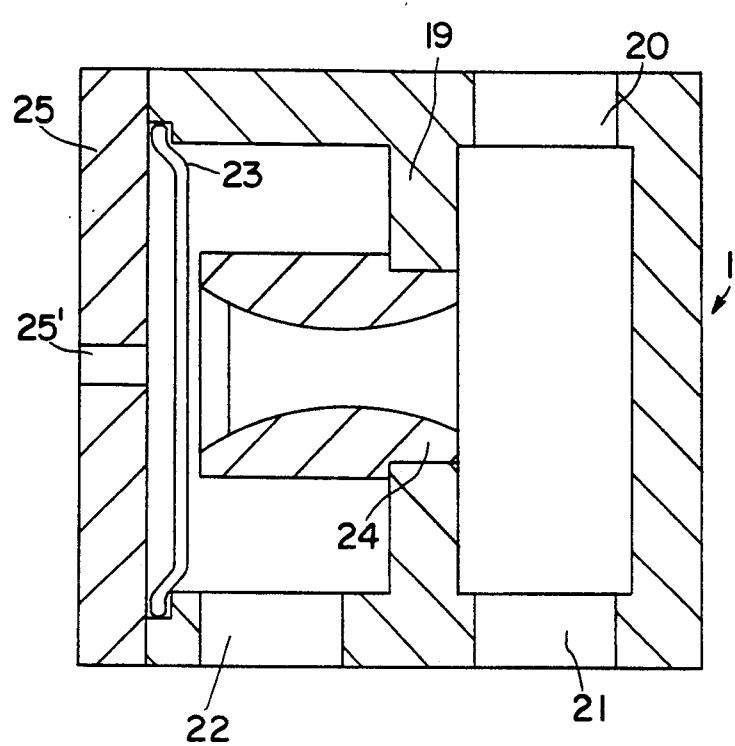
FIG. 4 is a cross-sectional view of the exhalation valve of the inspiratory airway.

The exhalation valve 1 of the inspiratory airway illustrated in FIG. 4 includes a main body 19 with three openings, an entry opening 20 for the air/oxygen mixture, an exit opening 21 for the inspiratory tube, and a third exhalation opening 22 whenever the pressure in the system surpasses the preset pressure thus allowing the mixture to be discharged into the environment. The pressing control is achieved by pressurizing a flexible diaphragm 23 over a nozzle 24 where the diaphragm is fit. The diaphragm will open nozzle 24 whenever the pressure on the side of the inspiratory airway exceeds the pressure exerted by the pressure control valves 10, 11, linked to opening 25' in base 25 of the exhalation valve 1.

Figure 5:
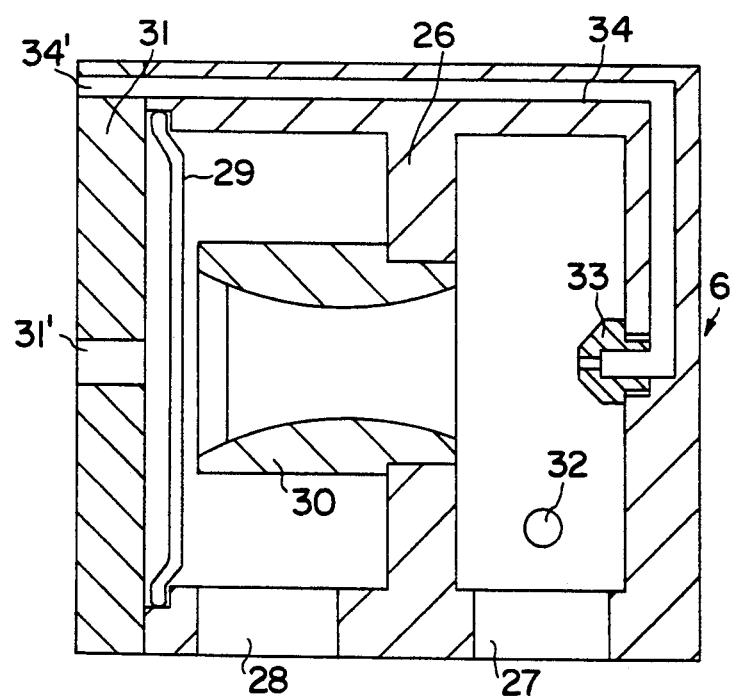
FIG. 5 is a cross-sectional view of the exhalation valve of the expiratory airway.

The exhalation valve 6 of the expiratory airway, illustrated in FIG. 5, includes a main body 26, and two openings, an entry opening 27 for the expiratory tube and another opening 28 for exhalation. The pressure control is made in the same way as with valve 1, through the fitting of a diaphragm 29 over a nozzle 30.

The diaphragm 29 is pressurized through the pressure control valves 10, 11, linked to opening 31' in base 31 of the exhalation valve 6. Contrary to the exhalation valve 1, the exhalation valve 6 includes a laminar flow device whose purpose is to decrease the turbulence of the exhaled gases in order to achieve a higher stability in the pressure control. This laminar flow device includes a cylinder 32 introduced transversely relative to the section of the entry opening 27. The adherence of the flow to the cylindrical surface promotes both a flow redirectioning and laminar flow. In addition, valve 6 includes an injector 33 fed by the pneumatic control module 8 linked to inlet opening 34' to provide continuous flow through route 34 within the body of the valve. The stream created by the injector is directed to a nozzle 30 where the diaphragm is fitted. The passage of the stream through the nozzle generates a subatmospheric pressure (venturi system) which helps in the exhalation of the gases, thus eliminating the occurrence of residual pressure, even at high flow rates.

The union of the laminar flow and venturi functions facilitates a more precise control of the working pressures. Moreover, venturi promotes a pressure differential between valve 1 and valve 6 which operates to compensate the pressure difference due to the resistances in the patient's system.

The use of a system having two exhalation valves 1, 6, one at the beginning of the inspiratory airway and the other at the end of the expiratory airway, eliminates the problems previously described using a system with a single valve, namely the accumulation of residual pressure, the influence of possible obstructions in the system, and the need for installing safety valves. The use of a second exhalation valve 1 to control pressure at the inspiratory airway, working in parallel with the expiratory airway valve 6, allows the device to cycle between set limits of expiratory and inspiratory pressures without interfering with the patient's ventilation or compromising the physical integrity of the patient.

The alarm system is coupled to the pressure monitoring system, independent of the microprocessor's electronic control module, thus avoiding an eventual failure in the microprocessor which may disable the alarm system.

Figure 6:
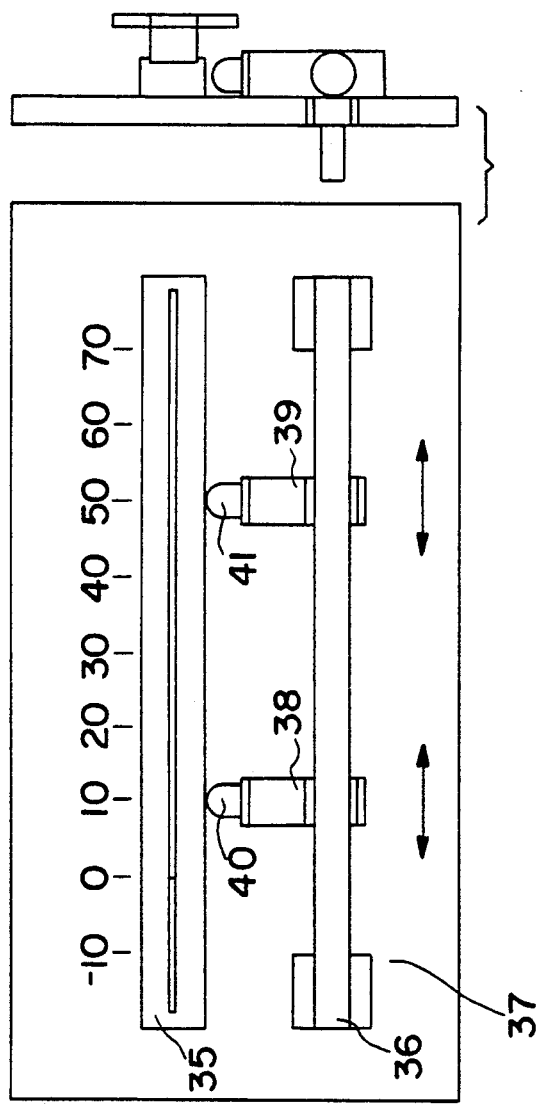
FIG. 6 shows the details of the monitoring and alarm system.

Referring to FIG. 6, pressure monitoring is facilitated by means of a piezoelectric transducer linked to the "Y" connection 4 through a tube 4'. The signal generated by the transducer (not shown) activates a bar display 35 with 80 light points linearly arranged. The pressure monitoring range extends from $-10$ cm $H_2O$ to 70 cm $H_2O$. The points ranging from $-10$ cm $H_2O$ to zero remain lit by default, and the application of a subatmospheric pressure will turn off the points proportionally. From zero on in a positive direction, the application of a positive pressure will proportionally light the points. In order to make easier the visualization, the lighted bar shows points which represents multiples of ten lighted points with a higher intensity.

The pressure monitoring system, which includes a piezoelectric transducer and a bar display, creates an alarm system through an optical coupling using the light of the display. This allows the placement of the alarm limits through two sliding cursors operatively coupled to the same scale of the display.

The system illustrated in FIG. 6 shows a light bar 35 fixed under a base of transparent material 37 where a printed graded scale ranging from $-10$ cm $H_2O$ to 70 cm $H_2O$ is printed. Two optical sensors 40 and 41 are positioned under the light bar 35 for detecting the minimal and maximal inspiratory pressures. These two sensors 40, 41 are fixed in different sliding cursors 38 and 39, thus allowing the positioning of the minimal and the maximal limits of the inspiratory pressure of the alarm system. The cursors 38 and 39 are capable of sliding over an axis 36 fixed to transparent base 37.

The minimal inspiratory pressure, as detected by the optical sensor 40, must surpass the minimal pressure setting during the inspiratory phase and must be below the minimal setting during the expiratory phase. The operation of the alarm for the minimal inspiratory pressure is linked to a timing circuit (not shown), selectively set for 3 to 20 seconds through a potentiometer (not shown) in the control panel. In this way, the alarm will be activated if within the time set by the potentiometer the sensor has not detected the rise and fall of the pressure through the set point.

With this system, it is possible to detect not only problems in pressure control during the controlled/intermittent mode, but also the occurrence of an apnea (absence of spontaneous respiratory movements) during the continuous pressure mode. In this event, there will be no pressure change, characteristic of spontaneous breathing, around the point set for minimal inspiratory pressure.

The maximal inspiratory pressure is the maximum limit which should not be surpassed. The sensor 41 located for the detection of the maximal inspiratory pressure will activate a sound alarm, inactivating the pilot solenoid 9 and activating the safety solenoid 9'. Thus, the exhalation valves 1, 6 are immediately opened allowing complete depressurization of a patient's system.

The ventilation device also has a "no break" module (not shown), including a rechargeable battery, load circuit, and automatic commuting system. Thus, in the event of an electrical power failure, or during transportation of the device, the device can continue to function.

We claim:

1. A ventilator device comprising:
   an inspiratory tube;
   an expiratory tube;
   a "Y" connector having a first port leading to a patient, a second port connected to one end of said inspiratory tube, and a third port connected to one end of said expiratory tube;
   a first valve coupled to the other end of said inspiratory tube and in fluid communication with a source of respiratory fluid, for controllably passing the fluid to the patient through said inspiratory tube; and
   a second valve, coupled to the other end of said expiratory tube and in fluid communication with the environment for controllably passing exhaled fluid from the patient to the environment; wherein
   said first valve includes means, responsive to fluid pressure in said inspiratory tube, for communicating said inspiratory tube to the environment when the pressure in said inspiratory tube exceeds a predetermined inspiratory pressure limit.

2. The ventilator as claimed in claim 1, wherein said second valve includes means, responsive to fluid pressure in said expiratory tube, for communicating said expiratory tube to the environment when the pressure in said expiratory tube exceeds a predetermined expiratory pressure limit.

3. The ventilator as claimed in claim 2, wherein said first and second valves each have fluid actuating means which sets the pressure at which the fluid in the respective tubes is communicated to the environment, said ventilator further comprising control means for controlling said first and second value actuating means, said control means including:
   an inspiratory control valve for setting the pressure limit at which said first valve couples said inspiratory tube to the environment; and an expiratory control valve for setting the pressure limit at which said second valve couples said expiratory tube to the environment.

4. The ventilator as claimed in claim 3, wherein said control valves are fed by an adjustable pressure regulating valve.

5. The ventilator as claimed in claim 3, wherein said fluid actuating means comprises a nozzle fitted with a diaphragm closing said nozzle under pressure from said control means.

6. The ventilator as claimed in claim 1, comprising a pressure monitoring system for monitoring the pressure in said inspiratory tube, said monitoring system comprising:
- a series of light emitting elements which progressively light along the series in response to increasing pressure in said inspiratory tube: and
- a pair of optical sensors located along said series of light emitting elements for detecting the pressure in said inspiratory tube falling below and above preset limits.

7. The ventilator as claimed in claim 6, wherein said control means is operated by an electronic module and pneumatic control through a solenoid valve.

8. The ventilator as claimed in claim 7, wherein said electronic module includes a microprocessor for controlling the inspiration time and the frequency of respiratory cycles, by regulating the opening and closing of said first and second valves through said solenoid valve.

9. The ventilator as claimed in claim 6, wherein said optical sensors are coupled to an alarm system which indicates out-of-limits conditions as detected by said optical sensors.

10. The ventilator as claimed in claim 6, wherein said series of light emitting elements define a lighted bar display, and said monitoring system include a pair of sliding cursors upon which said optical sensors are mounted, said cursors being slidable along said lighted bar display to set the positions of said optical sensors.

11. The ventilator as claimed in claim 1, comprising a moisturizing system coupled to said inspiratory tube between said first valve and the patient.

12. The ventilator as claimed in claim 1, wherein said second valve has an unobstructed gauged opening to the environment.

13. A ventilator device comprising:
- an inspiratory tube;
- an expiratory tube;
- a "Y" connector having a first port leading to a patient, a second port connected to one end of said inspiratory tube, and a third port connected to one end of said expiratory tube;
- a first valve coupled to the other end of said inspiratory tube and in fluid communication with a source of respiratory fluid, for controllably passing the fluid to the patient through said inspiratory tube; and
- a second valve, coupled to the other end of said expiratory tube and in fluid communication with the environment for controllably passing exhaled fluid from the patient to the environment, said second valve comprising:
- a main body;
- an opening in said main body for the admission of exhaled fluids from the patient, said opening having a cylinder transversally located to the direction of incoming fluid;
- a nozzle through which the exhaled fluid from the patient passes; and
- an injector directed toward said nozzle and fed through an opening in said main body by a source of pressurized fluid.

* * * * *